(12) United States Patent
Chackerian et al.

(10) Patent No.: US 7,560,530 B1
(45) Date of Patent: Jul. 14, 2009

(54) IL-33 RECEPTOR

(75) Inventors: Alissa A. Chackerian, Sunnyvale, CA (US); Robert A. Kastelein, Redwood City, CA (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 11/779,755

(22) Filed: Jul. 18, 2007

Related U.S. Application Data

(60) Provisional application No. 60/832,256, filed on Jul. 20, 2006, provisional application No. 60/835,250, filed on Aug. 3, 2006, provisional application No. 60/887,257, filed on Jan. 30, 2007.

(51) Int. Cl.
*C07K 14/715* (2006.01)
*G01N 33/53* (2006.01)

(52) U.S. Cl. .................................. 530/350; 435/7.2

(58) Field of Classification Search .................. None
See application file for complete search history.

(56) References Cited

U.S. PATENT DOCUMENTS

2005/0203046 A1   9/2005   Schmitz et al.

OTHER PUBLICATIONS

Mikayama et al. Proc. Natl. Acad. Sci. USAvol. 90, pp. 10056-10060.*
Voet et al. Biochemistry John Wiley & Sons, Inc., pp. 126-128 and 228-234.*
Braddock and Quinn (2004) *Nat. Rev. Drug Dis.* 3:330-339 "Targeting IL-1 in Inflammatory Disease: New Opportunities for Therapeutic Intervention".
Brunner et al. (2004) *Intensive Care Med* 30:1468-1473 "Increased levels of soluble ST2 protein and IgG1 production in patients with sepsis and trauma".
Casadio et al. (2001) *FEBS Lett* 499:65-68 "Model of interaction of the IL-1 receptor accessory protein IL-1RAcP with the IL-1β/IL-1R, complex".
Chackerian et al. (2007) *J. Immunol.* 179:2551-2555 "IL-1 receptor accessory protein and ST2 comprise the IL-33 receptor complex".
Cullinan et al. (1998) *J. Immunol.* 161:5614-5620 "IL-1 receptor accessory protein is an essential component of the IL-1 receptor".
Dinarello (2005) *Immunity* 23:461-464 "An IL-1 family member requires Caspase-1 processing and signals through the ST2 receptor".
Greenfeder et al. (1995) *J Biol Chem* 270:13757-13765 "Molecular cloning and characterization of a second subunit of the interleukin 1 receptor complex".
Huang et al. (1997) *Proc Natl Acad Sci USA* 94:12829-12832 "Recruitment of IRAK to the interleukin 1 receptor complex requires interleukin 1 receptor accessory protein".
Oshikawa et al. (2001) *Am J Respir Crit Care Med* 164:277-281 "Elevated soluble ST3 protein levels in sera of patients with asthma with an acute exacerbation".
Oshikawa et al. (2001) *Respiratory Med.* 95:532-533 "Acute eosinophilic pneumonia with increased soluble ST2 in serum and bronchoalveolar lavage fluid".
Schmitz et al. (2005) *Immunity* 23:479-490 "IL-33, an interleukin-1-like cytokine that signals via the IL-1 receptor-related protein ST2 and induces T helper type 2-associated cytokines".
Shimpo et al. (2004) *Ciculation* 109:2186-2190 "Serum levels of the interleukin-1 receptor family member ST2 predict mortality and clinical outcome in acute myocardial infarction".
Tajimo et al. (2003) *Chest* 124:1206-1214 "The increase in serum soluble ST2 protein upon acute exacerbation of idiopathic pulmonary fibrosis".
Towne et al. (2004) *J. Biol. Chem.* 279:13677-13688 "Interleukin (IL)-1F6, IL-1F8, and IL-1F9 signal through IL-1Rrp2 and IL-1RAcP to activate the pathway leading to NF-κB and MAPKs".
Trajkovic et al. (2004) *Cytokine & Growth Factor Reviews* 15:87-95 "T1/ST2—an IL-1 receptor-like modulator of immune responses".
Wesche et al. (1996) *FEBS Lett* 391:104-108 "Co-expression of MRNA for type I and type II interleukin-1 receptors and the IL-1 receptor accessory protein correlates to IL-1 responsiveness".
Wesche et al. (1997) *J. Biological Chemistry* 272:7727-7731 "The Interleukin-1 Receptor Accessory Protein (IL-1RAcP) is essential for IL-1-induced Activation of Interleukin-1 Receptor-associated Kinase (IRAK) and Stress-activated Protein Kinases (SAP Kinases)".

\* cited by examiner

*Primary Examiner*—Prema Mertz
(74) *Attorney, Agent, or Firm*—Schering-Plough Patent Department

(57) ABSTRACT

Provided herein are methods of modulating IL-33 activity, e.g., for the purpose of treating immune diseases and conditions, as well as methods of screening for compounds capable antagonizing IL-33 signaling.

4 Claims, 9 Drawing Sheets

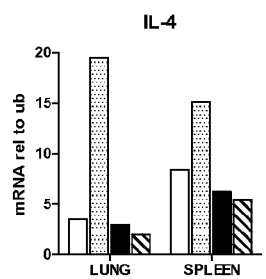
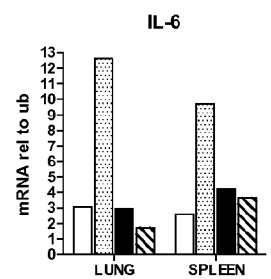
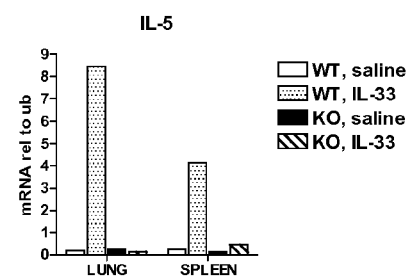
Figure 4A　　　　Figure 4B　　　　Figure 4C
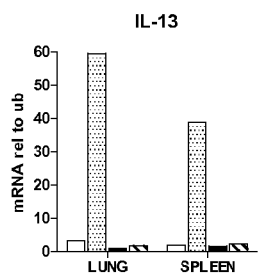
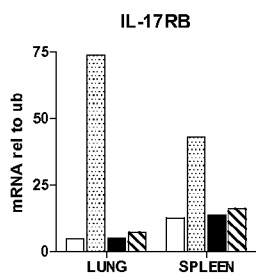
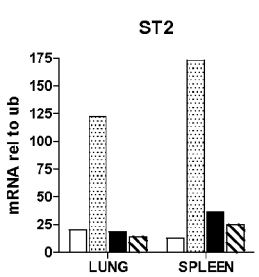
Figure 4D　　　　Figure 4E　　　　Figure 4F

IL-33 RECEPTOR

CROSS REFERENCE TO RELATED APPLICATIONS

The present claims priority to U.S. Provisional Patent Application Nos. 60/832,256 (filed Jul. 20, 2006), 60/835,250 (filed Aug. 3, 2006), and 60/887,257 (filed Jan. 30, 2007), the disclosures of which are hereby incorporated by reference in their entireties.

FIELD OF THE INVENTION

The present invention relates to methods for modulating IL-33 activity.

BACKGROUND OF THE INVENTION

The immune system protects individuals from infective agents, e.g., bacteria, multi-cellular organisms, as well as cancers. This system includes several types of lymphoid and myeloid cells such as monocytes, macrophages, dendritic cells (DCs), eosinophils, T cells, B cells, and neutrophils. These lymphoid and myeloid cells often produce signaling proteins known as cytokines. Immune response includes inflammation, i.e., the accumulation of immune cells systemically or in a particular location of the body. In response to an infective agent or foreign substance, immune cells secrete cytokines which, in turn, modulate immune cell proliferation, development, differentiation, or migration. Immune response sometimes results in pathological consequences, that is, inflammatory disorders. These inflammatory disorders, which involve immune cells and cytokines, include, e.g., psoriasis, rheumatoid arthritis (RA), Crohn's disease (CD), multiple sclerosis (MS), and atherosclerosis.

The interleukin-1 (IL-1) family of cytokines contributes to the pathology of inflammatory disorders and proliferative conditions, e.g., arthritis and cancer. There are 11 members of the IL-1 cytokine family. IL-1 cytokines bind to members of the IL-1 cytokine receptor family. There are ten members in the IL-1 receptor family, and IL-1 ligands typically require participation of two different IL-1 receptors to make up the cell surface complex. For example, IL-1α and IL-1β bind first to the cell surface receptor IL-1R1, and this IL-1/IL-1R1 complex subsequently binds to a second cell surface IL-1R family member, IL-1 Receptor accessory chain protein (IL-1RAcP). Binding of IL-1α or IL-1β to both receptor components is necessary to transduce the IL-1 signal.

IL-1 family members play a role in inflammatory conditions, e.g., rheumatoid arthritis, psoriasis, asthma, chronic obstructive pulmonary disorder (COPD), sepsis, and inflammatory bowel disorder (IBD). Rheumatoid arthritis (RA) is a common chronic inflammatory disorder characterized by degradation of joints, e.g., the synovial membrane, cartilage, and bone. IL-1 stimulates a number of cells involved in arthritic inflammation, e.g., fibroblasts, osteoclasts, chondrocytes, and neutrophils, which may show abnormal proliferation and release enzymes causing joint destruction.

Proliferative disorders are the second most common cause of death in the United States. Cytokines of the IL-1 family have been implicated in the control and pathology of proliferative disorders, i.e., cancer. IL-1 modulates progression through the cell cycle, e.g., by changing expression of cyclin-dependent kinases and cyclin-dependent kinase inhibitors. High doses of IL-1β promote tumor invasiveness, while low doses can promote immune eradication of tumors.

IL-33 exerts its biological effects via the receptor protein ST2 and induces T Helper Type 2-associated cytokines (Schmitz, J. et al., *Immunity* 23: 479-490 (2005)). In cells stimulated with IL-33, the signaling components MyD88, IRAK, IRAK4 and TRAF6 are recruited to ST2. In addition, IL-33 mediated signaling involves phosphorylation of IκBα and phosphorylation of the MAP kinases Erk1/2, p38 and JNK. $T_H2$ cells, but not $T_H1$ cells, respond to IL-33 stimulation with increased production of IL-5 and IL-13. IL-33 administration results in splenomegaly with significantly higher numbers of spleen eosinophils, mononuclear cells, and plasma cells, but not neutrophils. IL-33 administration also results in increased levels of blood eosinophils, lymphocytes and neutrophils. IL-33 administration also leads to induction of IL-4, IL-5 and IL-13 gene and protein expression in vivo. IL-33 administration also results in airway epithelial lining hypertrophy and mucous production, epithelial hyperplasia in the esophagus, and inflammatory infiltrates of eosinophils, neutrophils and mononuclear cells in the esophageal epithelium. In addition, IL-33 administration results in increased levels of serum IgE and IgA.

There remains an unmet need to treat inflammatory and immune disorders. Specifically, the need exists for improved compositions and methods of treatment for immune disorders related to IL-33 signaling in which reduction of IL-33 activity would provide therapeutic benefit.

SUMMARY OF THE INVENTION

We have previously shown that the orphan receptor ST2 is one of the components of the IL-33 receptor complex (Schmitz, J. et al., *Immunity* 23: 479-490 (2005)). It was thought that the receptor complex that binds IL-33 is a complex of ST2 and SIGIRR. See WO 2005/079844. Here, we explain that the second component of the IL-33 receptor complex is not SIGIRR, but is instead IL-1RAcP. Although no receptor promiscuity has been observed for the major IL-1 ligands (IL-1α and IL-1β exclusively bind to IL-1R1 and IL-1RAcP, and IL-18 binds exclusively to IL-18Rα and IL-18Rβ), we focused on IL-1RAcP after we were unsuccessful in finding the second IL-33 receptor among the orphan IL-1 receptors. Accordingly, the present invention provides that IL-33 signal transduction occurs through ST2 and IL-1RAcP.

In one aspect, the present invention provides methods of modulating (e.g. preventing, reducing or ameliorating) an immune disorder or condition, comprising inhibiting IL-33 signal transduction through ST2 and IL-1RAcP by administering to a subject in need thereof an effective amount of: (a) an antagonist of IL-33 binding to a complex of ST2 and IL-1RAcP, and/or (b) an antagonist of IL-1RAcP binding to a complex of IL-33 and ST2.

The present invention also provides methods of modulating blood cell counts, comprising inhibiting IL-33 signal transduction through ST2 and IL-1RAcP by administering to a subject in need thereof an effective amount of: (a) an antagonist of IL-33 binding to a complex of ST2 and IL-1RAcP, and/or (b) an antagonist of IL-1RAcP binding to a complex of IL-33 and ST2. Such modulation, e.g. may include increasing the count of platelets and/or decreasing the counts of one or more of total white blood cells, neutrophils, lymphocytes and eosinophils.

In various embodiments the antagonist comprises an antibody, or antigen-binding fragment thereof, that binds to IL-33, ST2, or a complex of IL-33 bound to ST2.

In other embodiments, the antagonist comprises an antibody, or antigen-binding fragment thereof, that binds to IL-1RAcP, a complex of IL-1RAcP and ST2, or a complex of IL-1RAcP, ST2 and IL-33. In some embodiments the antibody or fragment does not bind to IL-33 alone and/or does not bind to ST2 alone.

In yet another embodiment, the antibody or fragment does not bind to IL-1RAcP alone.

In one embodiment, the antibody or fragment thereof is a monoclonal, humanized, or fully human antibody. In another embodiment, the antibody or fragment is an Fab, an Fv fragment, or an F(ab')$_2$ fragment.

In some embodiments, the immune disorder or condition is selected from the group consisting of an innate response, asthma, an allergy, multiple sclerosis, inflammatory bowel disorder, arthritis, an infection, cancer, and a tumor. Exemplary arthritic conditions may be selected from the group consisting of rheumatoid arthritis, osteoarthritis, and psoriatic arthritis. Exemplary infections may be selected from the group consisting of an intracellular pathogen, a bacterium, a parasite and a virus. Exemplary intracellular pathogens may be selected from the group consisting of *Leishmania* sp., *Mycobacterium* sp., *Listeria* sp., *Toxoplasma* sp., *Schistosoma* sp.

In other embodiments, the immune disorder or condition is a $T_H1$-type response or a $T_H2$-type response.

In another aspect, the present invention provides methods and kits for the diagnosis of an immune condition or disorder. In one embodiment, the diagnostic method comprises determining the presence or level of one or more of IL-33, ST2, IL-1RAcP, a complex of IL-33 and ST2, a complex of ST2 and IL-1RAcP and a complex of ST2, IL-1RAcP and IL-33 in a sample from a subject, and comparing that level to the levels in non-diseased tissues, subjects that are known to have the immune condition or disorder, and/or subjects that are known not to have the immune condition or disorder. In one embodiment, the presence or level of a complex of IL-33 and ST2 is detected. In one embodiment the detection involves use of a binding compound comprising a detectable label, e.g. an antibody or antigen-binding fragment thereof. In another embodiment, the invention involves kits to perform the diagnostic methods of the invention, comprising: a compartment; a detectably-labeled molecule, such as an antibody, that binds one or more of IL-33, ST2, IL-1RAcP, a complex of IL-33 and ST2, a complex of ST2 and IL-1RAcP and a complex of ST2, IL-1RAcP and IL-33; and, optionally, instructions for use. In one embodiment, the detectably-labeled molecule binds to a complex of IL-33 and ST2.

In another aspect, the present invention provides an isolated and purified complex of ST2 and IL-1RAcP, optionally further comprising IL-33, and sequence variants thereof. In one embodiment the ST2, IL-1RAcP and IL-33 are human proteins. In other embodiments, the invention provides such complexes comprising polypeptide having 70%, 80%, 90%, 95%, 98% or 100% sequence identity with a naturally occurring human ST2, IL-1RAcP or IL-33 protein. In one aspect, the invention provides methods of making these isolated and purified complexes, comprising mixing two or more of the proteins and allowing said complex to form.

In yet another aspect, the present invention provides in vitro methods of determining whether a test compound is an antagonist of IL-33 binding to a complex of ST2 and IL-1RAcP, and/or IL-1RAcP binding to a complex of IL-33 and ST2, comprising an assay selected from the group consisting of a) an NF-κB-dependent reporter gene expression assay, b) an MyD88 IRAK, IRAK4 or TRAF6 recruitment assay, c) an Erk1/2, p38, IκBα or JNK phosphorylation assay, d) an NF-κB, Erk1/2 or p38 phosphorylation assay in cells that naturally express ST2, e) an IL-13, IL-6 or IL-5 expression assay, and f) an IL-6 production assay in mouse mast cell line WTMC. In some embodiments, the test compound is determined to be an antagonist if it reduces the activity of IL-33 in the assay when compared to an assay run without the test compound.

BRIEF DESCRIPTION OF THE DRAWINGS

FIGS. 4A-4F show that, unlike wild-type (WT) mice, IL-1RAcP deficient (KO) mice do not upregulate $T_H2$ cytokine or cytokine receptor genes in response to IL-33 administration

DETAILED DESCRIPTION OF THE PREFERRED EMBODIMENTS

Figure 1A:
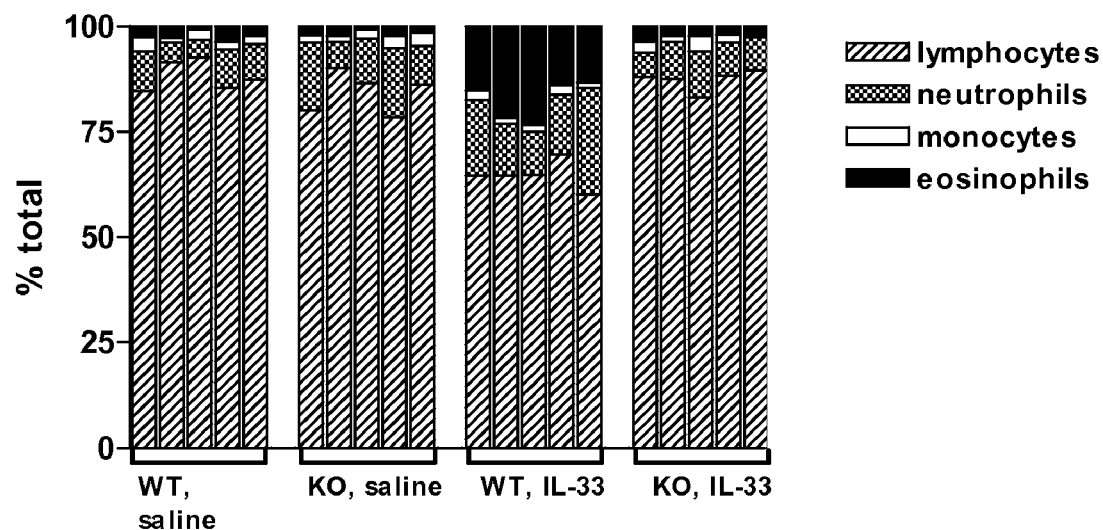
FIG. 1 shows that IL-33 administration increases the percentage of eosinophils found in the blood of wild-type (WT) mice, but not IL-1RAcP deficient (KO) mice. Individual data bars represent separate experimental animals, with one experiment involving five animals (FIG. 1A) and another involving three animals (FIG. 1B).

As used herein, including the appended claims, the singular forms of words such as "a," "an," and "the," include their corresponding plural references unless the context clearly dictates otherwise.

"Administering" refers to the delivery to an animal, human, subject, cell, tissue, organ, or biological fluid of an exogenous composition, pharmaceutical, therapeutic, or diagnostic agent, e.g. an agent containing an antagonist of IL-33 signal transduction through ST2 and IL-1RAcP. In one embodiment, "administering" refers to delivery to a subject. In another embodiment, "administering" refers to delivery to a human subject.

An "antagonist of IL-33 binding to a complex of ST2 and IL-1RAcP" is a molecule that inhibits IL-33 binding to a complex of ST2 and IL-1RAcP. An "antagonist of IL-1RAcP binding to a complex of IL-33 and ST2" is a molecule that inhibits binding of IL-1RAcP to a complex of IL-33 and ST2. In one embodiment, the antagonist is an antibody, such as a polyclonal antibody, a monoclonal antibody, a humanized antibody, or a human antibody. In another embodiment, the antagonist is an antibody fragment, such as a Fab, an Fv fragment, or a F(ab')$_2$ fragment.

In another embodiment, the antibody or fragment thereof specifically binds to (a) IL-33, (b) IL-1RAcP, (c) ST2, (d) a complex of ST2 bound to IL-1RAcP, (e) a complex of IL-33 bound to ST2, or (f) a complex of IL-33, ST2 and IL-1RAcP.

In one embodiment, an "effective amount" of the antagonist of IL-33 signal transduction through ST2 and IL-1RAcP means an amount sufficient to ameliorate a symptom or sign of a disorder or physiological condition, or an amount sufficient to permit or facilitate the diagnosis of a disorder or physiological condition. An effective amount for a human or veterinary subject may vary depending on factors such as the condition being treated, the overall health of the subject, the method route and dose of administration and the severity of side affects. In one embodiment, an effective amount is the maximal dose or dosing protocol that avoids significant side effects or toxic effects. The effect will result in an improvement of a diagnostic measure, parameter, or detectable signal by at least 5%, 10%, 20%, 30%, 40%, 50%, 60%, 70%, 80%, or 90%, where 100% is defined as the diagnostic parameter shown by a normal subject (see, e.g., Maynard, et al., *A Handbook of SOPs for Good Clinical Practice*, Interpharm Press, Boca Raton, Fla. (1996); Dent, *Good Laboratory and Good Clinical Practice*, Urch Publ., London, UK (2001)).

In another embodiment, an "effective amount" of the antagonist of IL-33 signal transduction through ST2 and IL-1RAcP means an amount sufficient to inhibit IL-33 signal transduction through ST2 and IL-1RAcP.

"Inhibiting IL-33 signal transduction through ST2 and IL-1RAcP" means that the degree to which IL-33 stimulates signal transduction through ST2 and IL-1RAcP is diminished in the presence of an antagonist, relative to the degree to which IL-33 stimulates signal transduction through ST2 and IL-1RAcP in the absence of the antagonist.

To examine the extent of inhibition, a sample is treated with a potential inhibitor and is compared to a control sample without the inhibitor. Control samples, i.e., not treated with antagonist, are assigned a relative activity value of 100%. Inhibition is achieved when the activity value relative to the control is about 90%, 85%, 80%, 75%, 70%, 65%, 60%, 55%, 50%, 45%, 40%, 35%, 30%, 25%, or 20% or less.

An endpoint in inhibition may comprise a predetermined quantity or percentage of, e.g., an indicia of inflammation, oncogenicity, or cell degranulation or secretion, such as the release of a cytokine. An endpoint of inhibition is generally 75%, 50%, 25%, or 10% of the control or less.

Inhibition of IL-33 signal transduction through ST2 and IL-1RAcP can be determined by assaying for IL-33 signal transduction in an in vitro assay. One in vitro assay that can be used is an NF-κB-dependent reporter assay (Schmitz, J. et al., *Immunity* 23: 479-490 (2005)). In this assay, cells, e.g., HEK293FT cells, are transfected with either a mock expression vector or with an expression vector encoding ST2 in conjunction with an NF-κB-driven reporter gene expression product, e.g., green fluorescent protein (GFP). Cells are incubated with IL-33 alone, or with IL-33 and a test molecule that is being tested for antagonistic activity. Cells are then analyzed for reporter gene expression product, e.g., by fluorescence activated cell sorting (FACS®). If IL-33 treated cells exhibit reduced reporter gene expression after incubation with the test molecule, the test molecule is an antagonist of IL-33 binding to the IL-1RAcP receptor complex.

Another reporter gene expression product that can be used is luciferase. In this assay, cellular extracts are assayed for NF-κB-driven luciferase expression in response to incubation with IL-33, and with or without a test molecule, i.e. a putative inhibitor of IL-33 signal transduction.

Another in vitro assay that can be performed is to assay for MyD88 IRAK, IRAK4, or TRAF6 recruitment (Schmitz, J. et al., *Immunity* 23: 479-490 (2005)). In this assay, cells, e.g., HEK293FT cells, are transfected with either a mock expression vector or with an expression vector encoding ST2, and incubated with IL-33. In the control experiment, no test molecule is added to the incubation. In the test experiment, the molecule to be tested for its ability to inhibit IL-33 signal transduction is added. Cellular extracts are immunoprecipitated with an anti-ST2 antibody, followed by Western analysis with anti-MyD88, IRAK, IRAK4, or TRAF6 antibodies. A decrease in expression of MyD88, IRAK, IRAK4, or TRAF6 in extracts from IL-33 treated cells when incubated with the test molecule indicates that the test molecule is an antagonist of IL-33 binding to the IL-1RAcP receptor complex.

Another in vitro assay that can be performed is to assay for phosphorylation of Erk1/2, p38, IκBα, or JNK (Schmitz, J. et al., *Immunity* 23: 479-490 (2005)). In this assay, cells, e.g., HEK293FT cells, are transfected with either a mock expression vector or with an expression vector encoding ST2, and incubated with IL-33. In the control experiment, no test molecule is added to the incubation. In the test experiment, the molecule to be tested for its ability to inhibit IL-33 signal transduction is added. Cellular extracts are prepared and blotted with anti-phospho-Erk1/2, anti-phospho-p38, anti-phospho-IκBα, or anti-phospho-JNK antibodies. A decrease in the level of phosphorylated Erk1/2, p38, IκBα, or JNK in extracts from IL-33 treated cells when incubated with the test molecule indicates that the test molecule is an antagonist of IL-33 binding to the IL-1RAcP receptor complex.

Another in vitro assay that can be performed is to assay for phosphorylation of NF-κB, Erk1/2 or p38 in cells that naturally express ST2, e.g., mouse mast cells (WTMC) (Schmitz, J. et al., *Immunity* 23: 479-490 (2005)). In the control experiment, WTMC cells are incubated with IL-33 but no test molecule is added to the incubation. In the test experiment, cells are incubated with IL-33 and the molecule to be tested for its ability to inhibit IL-33 signal transduction. Cell lysates are separated by SDS-PAGE and electroblotted. Cellular extracts are blotted with anti-NF-κB, anti-phospho-Erk1/2, or anti-phospho-p38 antibodies. A decrease in the level of phosphorylated NF-κB, Erk1/2, or p38 in extracts from IL-33 treated cells when incubated with the test molecule indicates that the test molecule is an antagonist of IL-33 binding to the IL-1RAcP receptor complex.

Another in vitro assay that can be performed is to assay expression of IL-5 or IL-13 in $T_H2$ cells (Schmitz, J. et al., *Immunity* 23: 479-490 (2005)). In the control experiment, $T_H2$ cells are incubated with IL-33 but no test molecule is added to the incubation. In the test experiment, $T_H2$ cells are incubated with IL-33 and the molecule to be tested for its ability to inhibit IL-33 signal transduction. Supernatants are analyzed for IL-5 and IL-13 production. A decrease in the level of IL-5 or IL-13 in supernatant from IL-33 treated cells when incubated with the test molecule indicates that the test molecule is an antagonist of IL-33 binding to the IL-1RAcP receptor complex.

Another in vitro assay that can be used to determine whether a molecule is an antagonist of IL-33 binding is to determine the effect of a test molecule on IL-33-induced production of IL-6 in the mouse mast cell line WTMC. A decrease in the level of IL-6 production by IL-33 treated cells when incubated with the test molecule indicates that the test molecule is an antagonist of IL-33 binding to the IL-1RAcP receptor complex.

In vivo assays that can be used to determine whether a molecule is an antagonist of IL-33 binding to the IL-1RAcP receptor complex is to determine the effect of a test molecule on the influence of IL-33 administration on spleen size, spleen cells (e.g., mononuclear cells, eosinophils, and plasma cells), blood cell count (e.g., eosinophils, lymphocytes or neutrophils) (Schmitz, J. et al., *Immunity* 23: 479-490 (2005)). A decrease in the effect of IL-33 after administration of IL-33 and the test molecule on an in vivo endpoint, relative to the effect of IL-33 alone, indicates that the test molecule is an antagonist of IL-33 binding to the IL-1RAcP receptor complex.

In a one embodiment, the antagonist that is assayed for in the above-described assays is an antibody.

"Expression" refers to a measure of mRNA or polypeptide encoded by a specific gene. Units of expression may be a measure of, e.g., the number of molecules of mRNA or polypeptide/mg protein, the number of molecules of mRNA or polypeptide/cell, in measurements of expression by cell, tissue, cell extract, or tissue extract. The units of expression may be relative, e.g., a comparison of signal from control and experimental mammals or a comparison of signals with a reagent that is specific for the mRNA or polypeptide versus with a reagent that is non-specific.

"Immune condition" or "immune disorder" encompasses, e.g., pathological inflammation, an inflammatory disorder, and an autoimmune disorder or disease. "Immune condition" also refers to infections, persistent infections, and proliferative conditions, such as cancer, tumors, and angiogenesis.

In one embodiment, the immune disorder or immune condition is selected from the group consisting of an innate response, asthma, allergy, multiple sclerosis, inflammatory bowel disorder, arthritis, an infection, cancer, and a tumor. In another embodiment, the arthritis is selected from the group consisting of rheumatoid arthritis, osteoarthritis, and psoriatic arthritis. In another embodiment, the immune disorder or condition comprises a $T_H1$-type response or a $T_H2$-type response.

"Infection" refers to a disorder resulting from a pathogen, microbe, bacterium, parasite, virus, and the like. In one embodiment, the infection is caused by an organism selected from the group consisting of a bacterium, a parasite, and a virus. In another embodiment, the infection is caused by an organism selected from the group consisting of *Leishmania* sp., *Mycobacterium* sp., *Listeria* sp., *Toxoplasma* sp., *Schistosoma* sp., and a respiratory virus.

"Inflammatory disorder" means a disorder or pathological condition where the pathology results, in whole or in part, from, e.g., a change in number, change in rate of migration, or change in activation, of cells of the immune system. Cells of the immune system include, e.g., T cells, B cells, monocytes or macrophages, antigen presenting cells (APCs), dendritic cells, microglia, NK cells, NKT cells, neutrophils, eosinophils, mast cells, or any other cell specifically associated with the immunology, for example, cytokine-producing endothelial or epithelial cells.

"IL-1RAcP" means the Interleukin-1 Receptor Accessory Protein. IL-1RAcP is further described at online Mendelian Inheritance in Man (OMIM) entry 602626 and Gene ID No. 3556, and exemplary naturally occurring sequences for human IL-1RAcP are found at GenBank Accession Nos. NP_608273 (SEQ ID NO: 1) and NP_002173 (SEQ ID NO: 2), all of which are available through the National Center for Biotechnology Information (NCBI) website.

"IL-33 receptor complex" refers to the specific binding of ST2 to IL-1RAcP to form a protein complex that itself specifically binds to IL-33 and transduces the IL-33 signal from the cell surface to the cell interior.

"IL-33/ST2 complex" refers to the specific binding of IL-33 and ST2 to form a protein complex that itself specifically binds to IL-1RAcP. IL-33 is further described at OMIM entry 608678 and Gene ID No. 90865, and an exemplary naturally occurring sequence for human IL-33 (SEQ ID NO: 3) is found at GenBank Accession No. AY905581, all of which are available through the NCBI website. See also Schmitz et al. (2005) Immunity 23: 479-490.

An "isolated and purified" complex, such as an isolated and purified complex of ST2 and IL-1RAcP, optionally further comprising IL-33, is an in vitro complex that is isolated and purified from its natural source. Specifically, an isolated and purified complex does not encompass complexes as they form in nature. Such complexes may be formed, e.g., by mixture of two or more purified proteins, or by mixture of one purified protein with a cell extract or biological sample, or by the purification of a complex from a natural source.

"IL-33 signal transduction through ST2 and IL-1RAcP" refers to the molecular events that occur when IL-33, ST2 and IL-1RAcP form a protein complex. In one embodiment, the IL-33 signal transduction refers to recruitment of one or more of MyD88, IRAK, IRAK4, and TRAF6 to ST2 in response to the formation of a complex of IL-33, ST2, and IL-1RAcP. In another embodiment, IL-33 signal transduction refers to phosphorylation of one or more of IκBκ, Erk1/2, p38 and JNK in response to the formation of a complex of IL-33, ST2, and IL-1RAcP. In another embodiment, IL-33 signal transduction refers to IL-5 or IL-13 secretion by $T_H2$ cells.

Specificity of binding refers to a binding interaction between a predetermined ligand and a predetermined receptor that enables one to distinguish between the predetermined ligand and other ligands, or between the predetermined receptor and other receptors. In one embodiment, the ligand is IL-33, and the receptor is ST2. In another embodiment, the ligand is IL-33, and the receptor is a protein complex of ST2 and IL-1RAcP. In another embodiment, the ligand is a protein complex of IL-33 and ST2, and the receptor is IL-1RAcP. In another embodiment, the ligand is an antibody or a fragment thereof that specifically binds to IL-33, IL-1RAcP, ST2, a complex of ST2 bound to IL-1RAcP, a complex of IL-33 bound to ST2, or a complex of IL-33, ST2 and IL-1RAcP.

A "pharmaceutical composition" comprises the active drug ingredient and one or more pharmaceutically acceptable excipients, carriers and/or diluents.

"Specifically binds" means a binding reaction that is determinative of the presence of a protein in a heterogeneous population of proteins and other biologics. For example, under designated conditions, one protein binds to another protein and does not bind in a significant amount to other proteins present in the sample. In various embodiments, an antibody or fragment thereof binds to its antigen with an affinity that is at least two fold greater, at least ten times greater, at least 20-times greater, or at least 100-times greater than the affinity to any other protein.

In various embodiments, an antibody, or fragment thereof, that specifically binds to IL-33, IL-1RAcP, ST2, a complex of ST2 bound to IL-1RAcP, a complex of IL-33 bound to ST2, or a complex of IL-33, ST2 and IL-1RAcP will bind with a $K_D$ of at least about $10^{-6}$ M, $10^{-7}$ M, $10^{-8}$ M, $10^{-9}$ M, $10^{-10}$ M, or $10^{-11}$ M or better (lower $K_D$).

"ST2" as used herein is synonymous with the T1/ST2 protein (also known as IL-1RL1). ST2 is further described at OMIM entry 601203 and Gene ID No. 9173, and exemplary naturally occurring sequences for human ST2 are found at GenBank Accession Nos. NP_003847 (SEQ ID NO: 4) and NP_057316 (SEQ ID NO: 5), all of which are available through the NCBI website.

"ST2/IL-1RAcP complex" refers to the specific binding of ST2 and IL-1RAcP to form a protein complex that itself specifically binds IL-33.

Purification of antigen is not necessary for the generation of antibodies. Immunization can be performed by DNA vector immunization, see, e.g., Wang, et al. *Virology* 228:278-284 (1997). Alternatively, animals can be immunized with cells bearing the antigen of interest. Splenocytes can then be isolated from the immunized animals, and the splenocytes can fused with a myeloma cell line to produce a hybridoma (Meyaard et al., *Immunity* 7:283-290 (1997); Wright et al., *Immunity* 13:233-242 (2000); Preston et al., *Eur. J. Immunol.* 27:1911-1918 (1997)). Resultant hybridomas can be screened for production of the desired antibody by functional assays or biological assays, that is, assays not dependent on possession of the purified antigen. Immunization with cells may prove superior for antibody generation than immunization with purified antigen (Kaithamana et al., *J. Immunol.* 163:5157-5164 (1999)).

Any suitable method can be used to elicit an antagonist antibody with the desired biologic properties. It may be desirable to prepare monoclonal antibodies (mAbs) from mammalian hosts such as mice, rodents, primates, humans, etc. Techniques for preparing such monoclonal antibodies may be found in, e.g., Stites et al. (eds.) BASIC AND CLINICAL IMMUNOLOGY (4th ed.) Lange Medical Publications, Los Altos, Calif., and references cited therein; Harlow and Lane (1988) ANTIBODIES: A LABORATORY MANUAL CSH Press; Goding (1986) MONOCLONAL ANTIBODIES: PRINCIPLES AND PRACTICE (2d ed.) Academic Press, New York, N.Y. Thus, monoclonal antibodies may be obtained by a variety of techniques familiar to researchers skilled in the art. Typically, spleen cells from an animal immunized with a desired antigen are immortalized, commonly by fusion with a myeloma cell. See Kohler and Milstein (1976) *Eur. J. Immunol.* 6:511-519. Alternative methods of immortalization include transformation with Epstein Barr Virus, oncogenes, or retroviruses, or other methods known in the art. See, e.g., Doyle et al. (eds. 1994 and periodic supplements) CELL AND TISSUE CULTURE: LABORATORY PROCEDURES, John Wiley and Sons, New York, N.Y. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a antigen binding fragment thereof by screening a DNA library from human B cells according, e.g., to the general protocol outlined by Huse et al. (1989) *Science* 246:1275-1281.

Other suitable techniques involve selection of libraries of antibodies in phage or similar vectors. See, e.g., Huse et al. supra; and Ward et al. (1989) *Nature* 341:544-546. The polypeptides and antibodies of the present invention may be used with or without modification, including chimeric or humanized antibodies. Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced, see Cabilly U.S. Pat. No. 4,816,567; and Queen et al. (1989) *Proc. Natl. Acad. Sci. USA* 86:10029-10033; or made in transgenic mice, see Mendez et al (1997) *Nature Genetics* 15:146-156. See also Abgenix and Medarex technologies.

Any suitable non-human antibody can be used as a source for the hypervariable region of a humanized antibody. Sources for non-human antibodies include, but are not limited to, murine, Lagomorphs (including rabbits), bovine, and primates. For the most part, humanized antibodies are human immunoglobulins (recipient antibody) in which hypervariable region residues of the recipient are replaced by hypervariable region residues from a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues that are not found in the recipient antibody or in the donor antibody. These modifications are made to further refine antibody performance of the desired biological activity. For further details, see Jones et al. (1986) *Nature* 321:522-525; Reichmann et al. (1988) *Nature* 332:323-329; and Presta (1992) *Curr. Op. Struct. Biol.* 2:593-596.

Methods for recombinantly engineering antibodies have been described, e.g., by Boss et al. (U.S. Pat. No. 4,816,397), Cabilly et al. (U.S. Pat. No. 4,816,567), Law et al. (European Patent Application Publication No. 438310) and Winter (European Patent Application Publication No. 239400).

In one embodiment, the antagonist of the present invention is administered in a pharmaceutical composition. In another embodiment, the antagonist of the present invention is administered in a sterile composition.

To prepare pharmaceutical or sterile compositions, an active drug ingredient is mixed with one or more pharmaceutically acceptable carriers, excipients and/or diluents. A Pharmaceutical formulation can be prepared in the form of, e.g., a lyophilized powder, an aqueous solution, or a suspension. See, e.g., Hardman, et al., *Goodman and Gilman's The Pharmacological Basis of Therapeutics*, McGraw-Hill, New York, N.Y. (2001); Gennaro, *Remington: The Science and Practice of Pharmacy*, Lippincott, Williams, and Wilkins, New York, N.Y. (2000); Avis, et al. (eds.), *Pharmaceutical Dosage Forms: Parenteral Medications*, Marcel Dekker, NY (1993); *Excipient Toxicity and Safety*, Marcel Dekker, Inc., New York, N.Y. (2000).

Selecting an administration regimen for a therapeutic depends on several factors, including the serum or tissue turnover rate of the entity, the level of symptoms, the immunogenicity of the entity, and the accessibility of the target cells in the biological matrix. Preferably, an administration regimen maximizes the amount of therapeutic delivered to the patient consistent with an acceptable level of side effects. Accordingly, the amount of biologic delivered depends in part on the particular entity and the severity of the condition being treated. Guidance in selecting appropriate doses of antibodies is available. See, e.g., Wawrzynczak, *Antibody Therapy*, Bios Scientific Pub. Ltd, Oxfordshire, UK (1996); Kresina (ed.), *Monoclonal Antibodies, Cytokines and Arthritis*, Marcel Dekker, New York, N.Y. (1991); Bach (ed.), *Monoclonal Antibodies and Peptide Therapy in Autoimmune Diseases*, Marcel Dekker, New York, N.Y. (1993).

An antibody or fragment thereof can be provided by continuous infusion, or by doses at intervals. An antibody or fragment thereof may be administered intravenously, intramuscularly, or subcutaneously.

A preferred dose protocol is one involving the maximal dose or dose frequency that avoids significant undesirable side effects. In various embodiments, the total weekly dose is 0.05 µg/kg, 0.2 µg/kg, 0.5 µg/kg, 1 µg/kg, 10 µg/kg, 100 µg/kg, 0.2 mg/kg, 1.0 mg/kg, 2.0 mg/kg, 10 mg/kg, 25 mg/kg, 50 mg/kg or more.

An effective amount for a particular patient may vary depending on factors such as the condition being treated, the overall health of the patient, the method route and dose of administration and the severity of side affects (see, e.g., Maynard, et al., *A Handbook of SOPs for Good Clinical Practice*, Interpharm Press, Boca Raton, Fla. (1996); Dent, *Good Laboratory and Good Clinical Practice*, Urch Publ., London, UK (2001)).

Determination of the appropriate dose is made by the clinician, e.g., using parameters or factors known or suspected in the art to affect treatment or predicted to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced. Preferably, a biologic that will be used is derived from the same species as the animal targeted for treatment, thereby minimizing a humoral response to the reagent.

The present invention also provides a method of modulating blood cell counts, the method comprising administering an effective amount of an antagonist of IL-33 signal transduction through ST2 and IL-1RAcP. In one embodiment, the antagonist increases the count of platelets. In another embodiment, the antagonist decreases the counts of total white blood cells, neutrophils, lymphocytes, and/or eosinophils.

The present invention also provides methods and kits for the diagnosis of an immune condition or disorder. A method of diagnosis can comprise contacting a sample from a subject, e.g., a test subject, with an antibody or fragment thereof that specifically binds to (a) IL-33, (b) IL-1RAcP, (c) ST2, (d) a complex of ST2 and IL-1RAcP, (e) a complex of IL-33 and ST2, or (f) a complex of IL-33, ST2 and IL-1RAcP. The method can further comprise contacting a sample from a control subject, normal subject, or normal tissue or fluid from the test subject, with an antibody or fragment thereof. Moreover, the method can additionally comprise comparing the specific binding of the antibody or fragment thereof to the test subject with the specific binding of the composition to the normal subject, control subject, or normal tissue or fluid from the test subject. Expression or activity of a test sample or test subject can be compared with that from a control sample or control subject. A control sample can comprise, e.g., a sample of non-affected or non-inflamed tissue in a patient suffering from an immune disorder. Expression or activity from a control subject or control sample can be provided as a predetermined value, e.g., acquired from a statistically appropriate group of control subjects.

Kits for the diagnosis of an immune condition or disorder may comprise a compartment and a binding compound, e.g. an antibody or antigen-binding fragment thereof, that specifically binds to one or more components of IL-33 signal transduction through ST2 and IL-1RAcP. Such kits may optionally include instructions for use. In some embodiments the binding compound is detectably labeled.

The broad scope of this invention is best understood with reference to the following examples, which are not intended to limit the inventions to specific embodiments.

Many modifications and variations of this invention, as will be apparent to one of ordinary skill in the art can be made to adapt to a particular situation, material, composition of matter, process, process step or steps, to preserve the objective, spirit and scope of the invention. All such modifications are intended to be within the scope of the claims appended hereto without departing from the spirit and scope of the invention. The specific embodiments described herein are offered by way of example only, and the invention includes the full scope of equivalents to which such claims are entitled; and the invention is not to be limited by the specific embodiments that have been presented herein.

All citations herein are incorporated herein by reference to the same extent as if each individual publication, patent application, patent, database entry or other document was specifically and individually indicated to be incorporated by reference including all figures and drawings.

EXAMPLE 1

Animal Experiments

In order to determine whether IL-1RAcP is the second member of the receptor complex, wild-type (WT) and IL-1RAcP deficient (KO) mice were used. The wild-type (WT) mice used were strain B6; 129SF2/J (Jackson Laboratories). The IL-1RAcP deficient (KO) mice used were strain B6; 129S1-Il1rap$^{tm1/Rom1}$/J (Jackson Laboratories). The IL-1RAcP deficient mice have been genetically altered and do not have a functional IL-1RAcP receptor protein.

Wild-type and IL-1RAcP deficient mice were given daily intraperitoneal injections of saline or 2 micrograms of human IL-33 for six days. On day seven, the mice were sacrificed and analyzed for IL-33 responsiveness by several endpoints, as discussed in the following Examples. Blood eosinophilia was measured in blood smears. Serum and bronchoalveolar lavage (BAL) fluid were collected to quantitate cytokine levels and serum immunoglobulin (Ig) E levels. Lung and spleen tissue was collected to quantitate messenger RNA of key cytokines. Lung and small intestine tissue was analyzed for histological changes. Two replicate experiments were performed with either three or five mice per treatment group.

The following data show that IL-1RAcP deficient mice do not respond to IL-33 administration, indicating that IL-1RAcP is necessary to mediate the in vivo effects of IL-33. These results implicate IL-1RAcP as the second component of the IL-33 receptor.

EXAMPLE 2

Lack of Blood Eosinophilia in IL-1RAcP Deficient Mice

Figure 1B:
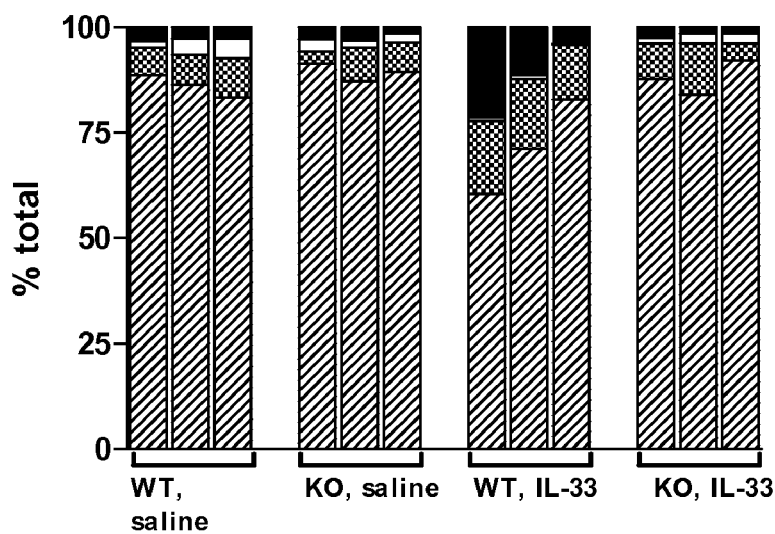

Tail blood was smeared onto glass slides, fixed in 95% ethanol, and stained by the Wright-Giemsa method. Cells were enumerated by microscope, and at least 300 cells were counted per mouse. The graphs in FIGS. 1A and 1B represent the two replicate experiments performed, involving five and three animals, respectively. IL-33 administration to wild-type mice dramatically increased the percentage of eosinophils found in the blood. However the percent of eosinophils in the blood of IL-33-treated IL-1RAcP deficient mice was not increased, and was similar to saline treated mice.

EXAMPLE 3

Lack of Goblet Cell Hyperplasia and Mucous Production in IL-1RAcP Deficient Mice Formalin-fixed, paraffin-embedded small intestines were stained by Periodic acid-Schiff. Wile-type mice, but not IL-1RAcP deficient mice, responded to IL-33 with increased goblet cell mucous production in the small intestine. A total of eight mice were examined per treatment condition. A similar finding was noted in the upper airways of the lung.

EXAMPLE 4

IL-1RAcP Deficient Mice Fail to Respond to IL-33 with Increased Production of IL-5

Figure 2A:
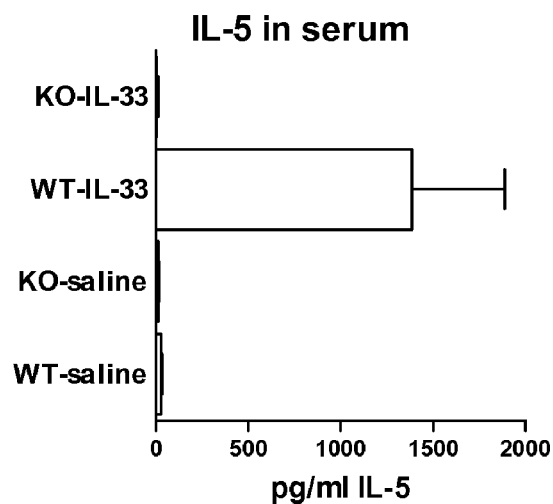
FIG. 2 shows that IL-33 administration increases IL-5 production in serum (FIG. 2A) and bronchioalveolar lavage (BAL) (FIG. 2B) in wild-type (WT) mice, but not in IL-1RAcP deficient (KO) mice.
Figure 2B:
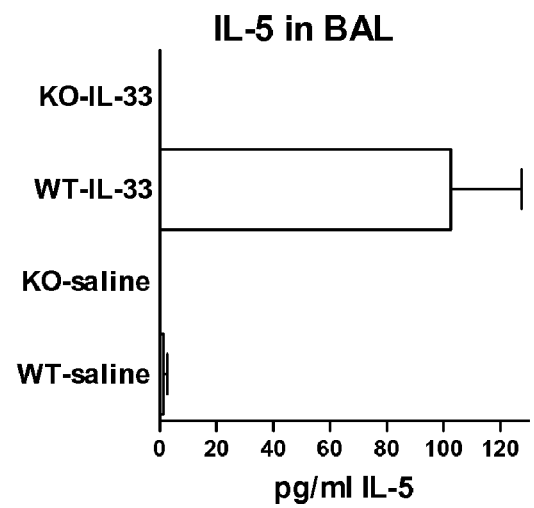

Serum and BAL fluid were analyzed for cytokine content by multiplex immunoassay. In both the serum (FIG. 2A) and BAL fluid (FIG. 2B), IL-33 treatment dramatically increased the production of IL-5 in wild-type mice, but not in IL-1RAcP deficient mice. The data are representative of two experiments.

EXAMPLE 5

Figure 3:
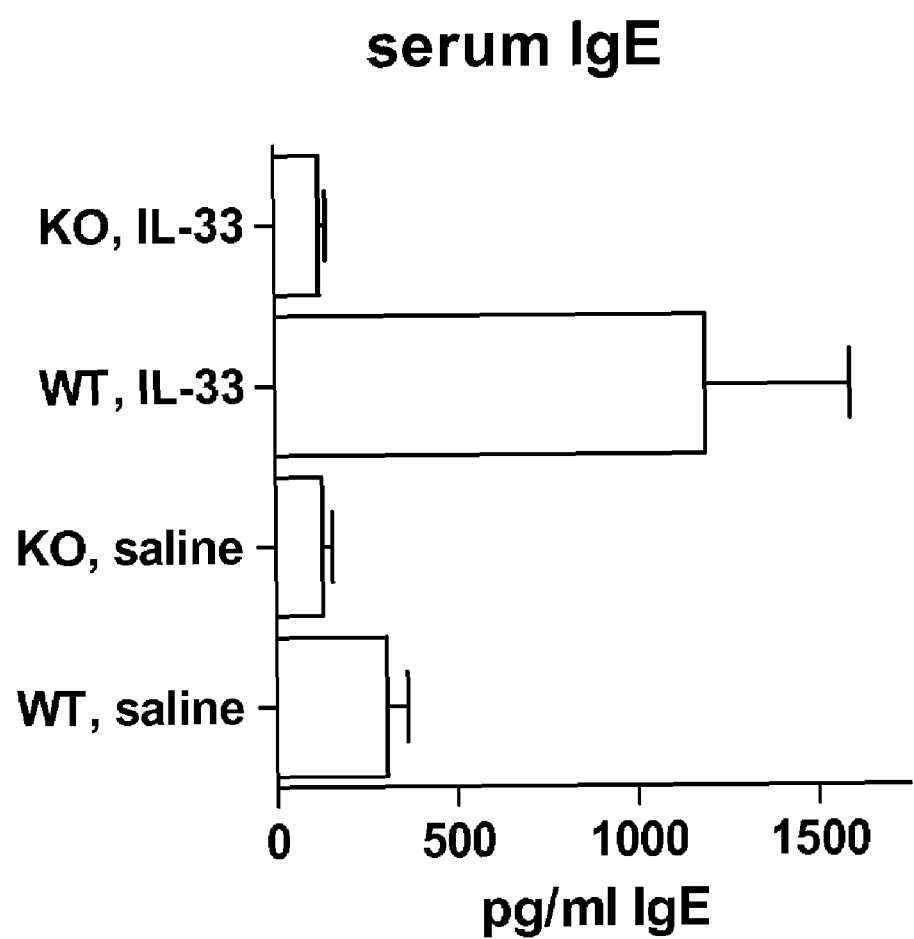
FIG. 3 shows that IL-33 administration increases serum IgE in wild-type (WT) mice, but not in IL-1RAcP deficient (KO) mice.

Serum Levels of IgE are Increased in Wild-Type but not IL-1RAcP Deficient Mice Serum IgE levels were measured by ELISA. IL-33 increased serum IgE in wild-type, but not in IL-1RAcP deficient mice (FIG. 3). The data are representative of two experiments.

EXAMPLE 6

IL-1RAcP Deficient Mice do not Upregulate $T_H2$ Cytokine Genes in Response to IL-33 Administration RT-PCR was performed on RNA obtained from snap-frozen spleen and lung tissue, and gene expression is shown in FIG. 4, relative to the levels of ubiquitin (ub) in the sample. IL-33 increased mRNA expression of the T helper 2 ($T_H2$) cytokines and cytokine receptors IL-4 (FIG. 4A), IL-5 (FIG. 4C), IL-6 (FIG. 4B), IL-13 (FIG. 4D), IL-17RB (FIG. 4E), and ST2 (FIG. 4F), in the lung and spleen of wild-type mice, but not in IL-1RAcP deficient ("KO") mice.

EXAMPLE 7

IL-33 Induces IL-6 Production in WTMC Cells

The mouse mast cell line WTMC (Wright, G. J., et al., *J. Immunol.* 171: 3034-3046 (2003)), expresses ST2 and responds to both human and mouse IL-33 in a dose dependent manner by producing IL-6. IL-33 activity can be blocked by preincubating the cells with a blocking rat anti-mouse ST2 antibody (MD Biosciences).

Figure 5:
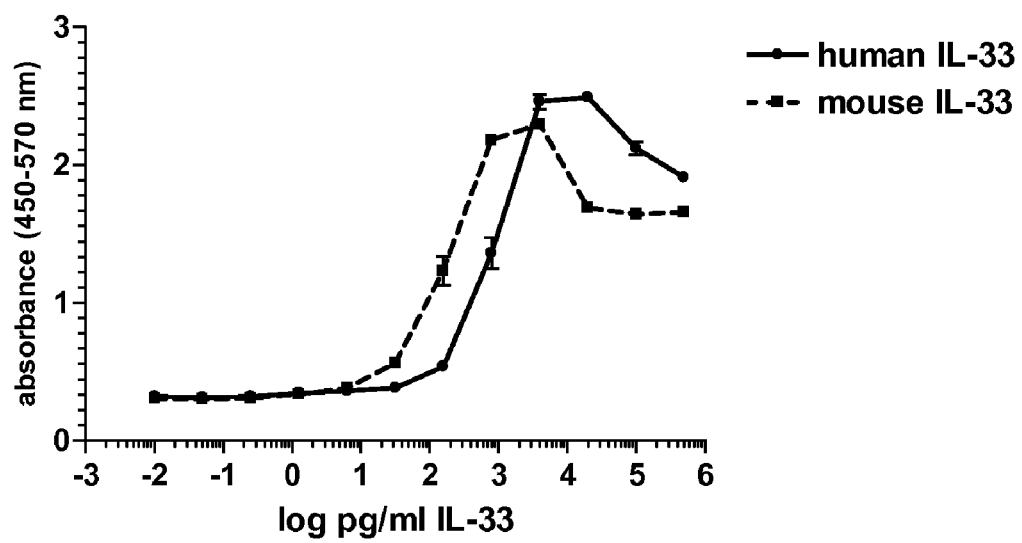
FIG. 5 shows that IL-33 induces IL-6 production from WTMC cells in a dose dependent manner.

$1 \times 10^5$ WTMCs were plated per well (96-well plate format) in RPMI 1640 w/L-glutamine containing 10% fetal calf serum, 1 mM Na-Pyruvate, 0.05 mM 2-mercapto-ethanol, 0.2 mM L-glutamine, 1×MEM non-essential amino acids, 1×PenStrep, 2.5 ng/ml mouse IL-3, and 2.5 ng/ml mouse IL-4. Cells were incubated for 24 hours with varying concentrations of mouse or human IL-33. Supernatants were assessed for IL-6 production by ELISA. As shown in FIG. 5, IL-33 induced IL-6 production in a dose dependent manner.

Figure 6:
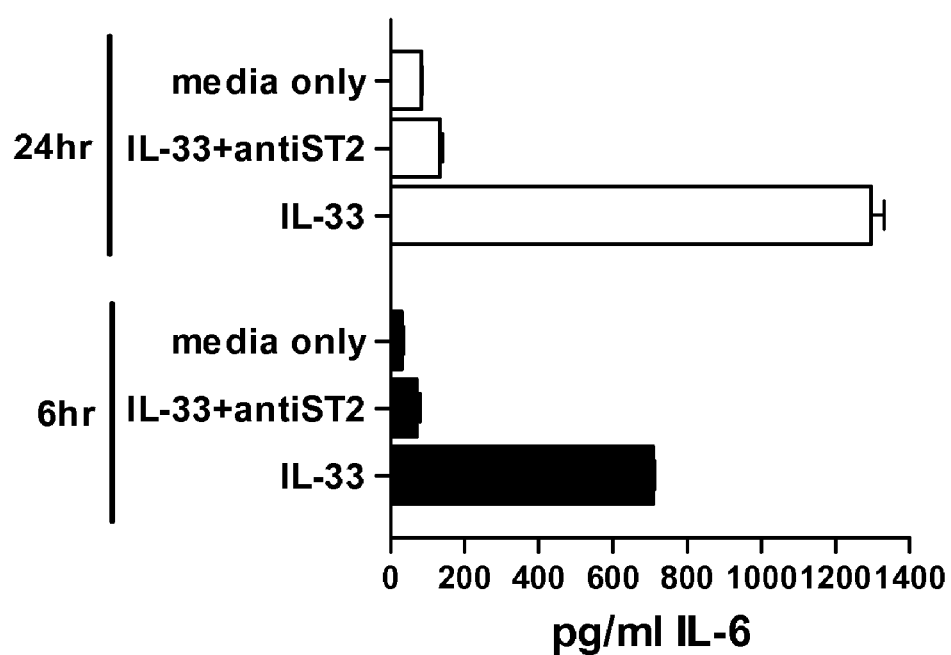
FIG. 6 shows that blocking ST2 prevents IL-33-induced IL-6 production in WTMC cells.

As shown in FIG. 6, a blocking rat anti-mouse ST2 antibody (MD Biosciences) prevented IL-33 induced production in WTMCs. Mast cells were seeded with into 24 well plates at $1 \times 10^6$ cells/well. Some cells were preincubated with anti-ST2 antibody (10 µg/ml) prior to the addition of IL-33 (50 ng/ml). Supernatants were collected after 6 and 24 hours and analyzed for cytokine production by multiplex immunoassay.

EXAMPLE 8

IL-1RAcP is Necessary for IL-33-Enhanced IL-5, IL-6, and IL-13 Production from $T_H2$ Cells CD4+ T cells were isolated from wildtype (B6; 129SF2/J) and IL-1RAcP knock-out (B6; 129S1-Il1rap$^{tm1/Rom1}$/J) mouse spleen and lymph nodes using the CD4+ T cell isolation kit (Miltenyi Biotec). To polarize towards a $T_H2$ phenotype, cells were cultured on anti-CD3 coated plates in the presence of 5 ng/ml IL-2, 10 ng/ml IL-4, 10 µg/ml anti-IFNγ, and 1 µg/ml anti-CD28 in complete RPMI for 4 days. Cells were then washed, and rested for 3 days in IL-2 (5 ng/ml) alone. Cells were then washed and stimulated with media alone, human IL-33 (50 ng/ml), or mouse IL-1β (10 ng/ml). Some cells were preincubated with anti-ST2 blocking antibody prior to cytokine addition. Supernatants were harvested after 24 hours and cytokine levels were measured using a multiplexed immunoassay (22-plex mouse cytokine premixed beads, Linco), and analyzed by Luminex® immunoassay.

Figure 7A:
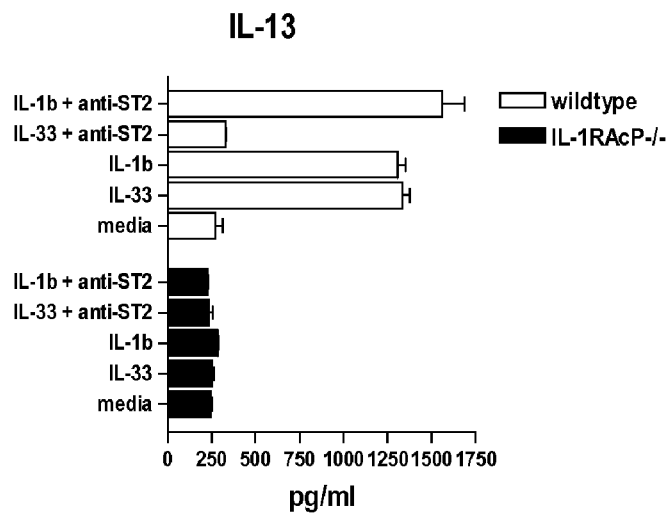
FIG. 7 shows that IL-1RAcP is necessary for IL-33-enhanced IL-13 (FIG. 7A), IL-6 (FIG. 7B), and IL-5 (FIG. 7C) production from $T_H2$ cells
Figure 7B:
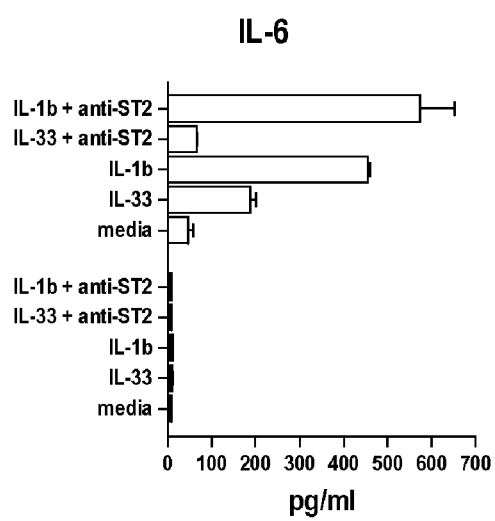
Figure 7C:
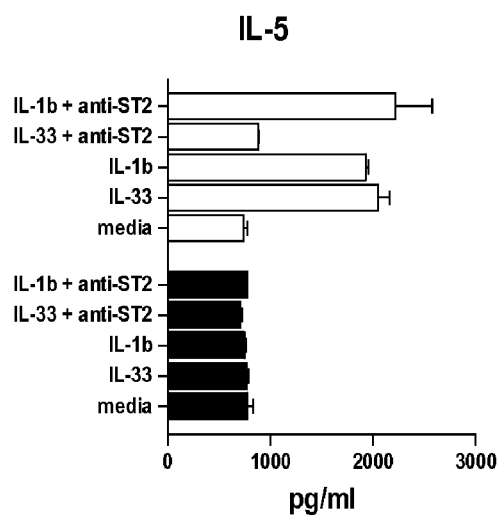

As shown in FIG. 7, both IL-1β and IL-33 enhanced the production of IL-13, IL-6, and IL-5 in wildtype, but not IL-1RAcP–/– $T_H2$ cells. The increased production of these cytokines in wildtype mice by IL-33 was blocked in the presence of anti-ST2 antibodies. Anti-ST2 did not block IL-1β-enhanced cytokine production.

EXAMPLE 9

Detection of the ST2/IL-33/IL-1RAcP Complex

Figure 8A:
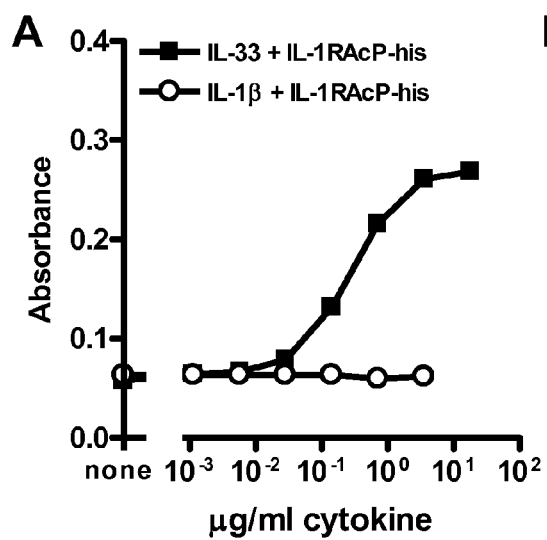
FIG. 8 shows the detection of the ST2/IL-33/IL-1RAcP complex, in which ST2 is immobilized on the plate in FIG. 8A and IL-1R1 is immobilized on the plate in FIG. 8B.
Figure 8B:
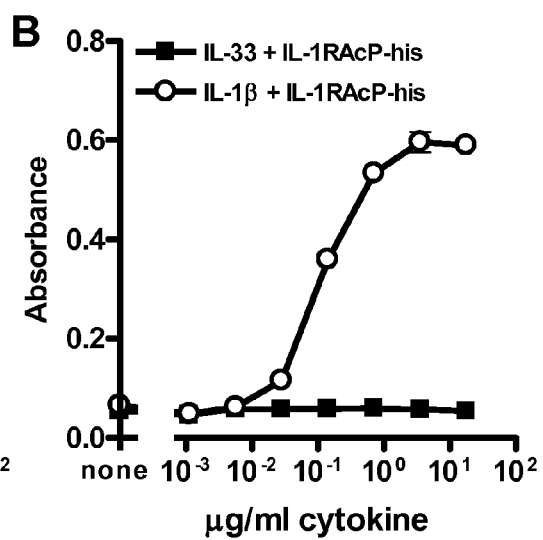

Murine IL-1 or IL-33 was titrated into plates containing soluble his6-tagged murine IL-1RAcP and plate-bound ST2-Fc (FIG. 8A) or IL-1R1-Fc (FIG. 8B). Peroxidase-conjugated anti-his6 was used as a detection antibody. Data is representative of 2 experiments. Data represent the mean+/–SEM of duplicate wells.

Receptor-ligand complex ELISA: 3 µg/ml murine ST2-Fc or IL-1R1-Fc fusion proteins (R&D Systems) in PBS were coated overnight onto MaxiSorp plates (Nunc). After washing, plates were incubated with 3 µg/ml recombinant his6-tagged murine IL-1RAcP and increasing concentrations of murine IL-33 or IL-1β in PBS/1% bovine serum albumin/0.05% Tween-20® polyoxyethylene sorbitan monolaurate for 1.5 hours. Plates were washed and incubated with anti-his6-peroxidase (Roche Diagnostics) for 1 hour, washed again, developed with TMB Peroxidase substrate (KPL), stopped with $H_2PO_4$, and read on a plate reader at 450-570 nm.

Although IL-1RAcP is required to mediate the effects of IL-33 in vivo and on Th2 cells, the possibility exists that this is due to an indirect rather than a direct interaction of IL-33 and IL-1RAcP. Therefore, we wished to detect formation of the ligand-receptor complex in vitro. In the IL-1 receptor complex, IL-1RAcP cannot bind IL-1 directly, rather it is hypothesized to interact with the complex of IL-1 and its primary receptor, IL-1R1. We are also unable to see a direct interaction of IL-33 with IL-1RAcP (not shown). However, we can detect a specific ST2/IL-33/IL-1RAcP complex by ELISA. We titrated IL-33 or IL-1β into wells containing plate-bound ST2 and soluble his6-tagged IL-1RAcP (FIG. 8A). We detect IL-33 receptor complex formation with an anti-his6 antibody as the concentration of IL-33, but not IL-1β, increases. Conversely, if the plates are coated with IL-1R1 instead of ST2, we detect IL-1 receptor complex formation with increasing amounts of IL-1β but not IL-33 (FIG. 8B). This result demonstrates that ST2, IL-33, and IL-1RAcP can form a ligand/receptor complex.

EXAMPLE 10

Dominant Negative IL-1RAcP Inhibits IL-33 Signaling

Signal transduction by IL-1RAcP in the IL-1 signaling cascade is mediated by its cytoplasmic Toll/IL-1 receptor (TIR) domain and involves recruitment of the adaptor MyD88 and activation of NF-κB. IL-33 uses the same signaling components as IL-1, including IRAK, IRAK4, MyD88, and TRAF6, leading to the activation of NF-κB and MAP kinases. MyD88 is required for IL-33 signaling, as MyD88−/− mice do not respond to IL-33 administration (data not shown). In order to investigate the contribution of IL-1RAcP to IL-33 signal transduction, we used a dominant negative form of IL-1RAcP that contains a stop codon before the TIR domain.

Figure 9:
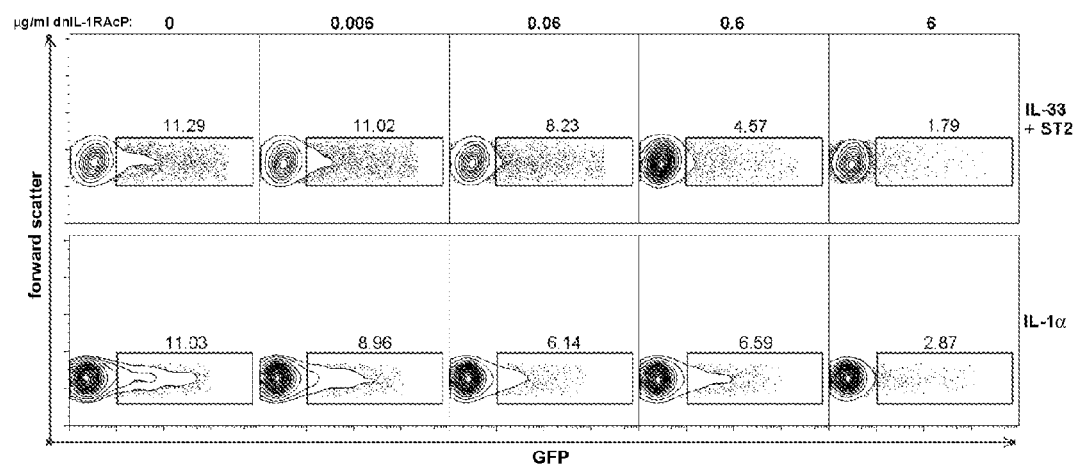
FIG. 9 shows that dominant negative IL-1RAcP inhibits IL-33 signaling.

As a positive control, HEK293FT cells, which endogenously express human IL-1R1 and IL-1RAcP, were transfected with 3 μg of a NF-κB-driven reporter gene construct (pNF-κB-hrGFP, Stratagene), and with increasing amounts of cMyc-tagged murine dominant negative (dn) IL-1RAcP construct. Cells were stimulated at 24 hours post-transfection with 20 ng/ml murine IL-1α (R&D Systems) for 24 hours, and analyzed for GFP expression by FACS® cell sorting. This control tests the ability of the dn IL-1RAcP to interact with the endogenous IL-1R1 and block IL-1α mediated downstream signaling. This interaction is reflected by the diminution of GFP expression when increasing amounts of the dn IL1-RAcP are transfected into control cells (FIG. 9, bottom row).

For experimental samples, HEK293FT cells were transfected with 11 g of a plasmid encoding murine ST2, 3 μg of the NF-κB-driven reporter gene construct, and with increasing amounts of cMyc-tagged murine dominant negative (dn) IL-1RAcP construct. Cells were stimulated at 24 hours post-transfection with 20 ng/ml murine IL-33 for 24 hours, and analyzed for GFP expression by FACS® cell sorting. Results of a typical experiment are provided at FIG. 9 (top row). This experimental system tests the ability of the dn IL-1RAcP to interact with murine ST2 and block IL-33 signaling. The addition of the dn IL-1RAcP caused a roughly dose-responsive decrease in IL-33-induced reporter gene expression, suggesting that ST2 uses IL-1RAcP as a second receptor to mediate IL-33 signal transduction.

---

What is claimed is:

1. An isolated and purified complex of human ST2 and human Interleukin-1 Receptor Accessory Protein (IL-1RAcP), wherein the human ST2 comprises the amino acid sequence of residues 19-556 of SEQ ID NO: 5, and the human IL-1RAcP comprises the amino acid sequence of residues 21-570 of SEQ ID NO: 2.

2. The isolated and purified complex of claim 1, further comprising human IL-33, wherein the human IL-33 comprises the amino acid sequence of residues 112-270 of SEQ ID NO: 3.

3. The isolated and purified complex of claim 1, wherein the complex is formed by mixing purified human ST2 and human IL-1RAcP polypeptides.

4. The isolated and purified complex of claim 1, wherein the complex is formed by mixing a purified human ST2 or human IL-1RAcP polypeptide with a cell extract or biological sample.

* * * * *

SEQUENCE LISTING

```
<160> NUMBER OF SEQ ID NOS: 5

<210> SEQ ID NO 1
<211> LENGTH: 356
<212> TYPE: PRT
<213> ORGANISM: Homo sapiens

<400> SEQUENCE: 1

Met Thr Leu Leu Trp Cys Val Val Ser Leu Tyr Phe Tyr Gly Ile Leu
1               5                   10                  15

Gln Ser Asp Ala Ser Glu Arg Cys Asp Asp Trp Gly Leu Asp Thr Met
            20                  25                  30

Arg Gln Ile Gln Val Phe Glu Asp Glu Pro Ala Arg Ile Lys Cys Pro
        35                  40                  45

Leu Phe Glu His Phe Leu Lys Phe Asn Tyr Ser Thr Ala His Ser Ala
    50                  55                  60

Gly Leu Thr Leu Ile Trp Tyr Trp Thr Arg Gln Asp Arg Asp Leu Glu
65                  70                  75                  80

Glu Pro Ile Asn Phe Arg Leu Pro Glu Asn Arg Ile Ser Lys Glu Lys
                85                  90                  95

Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
        115                 120                 125

Leu Glu Val Val Gln Lys Asp Ser Cys Phe Asn Ser Pro Met Lys Leu
    130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                165                 170                 175

Trp Tyr Met Gly Cys Tyr Lys Ile Gln Asn Phe Asn Asn Val Ile Pro
```

```
                180                 185                 190
Glu Gly Met Asn Leu Ser Phe Leu Ile Ala Leu Ile Ser Asn Asn Gly
            195                 200                 205

Asn Tyr Thr Cys Val Val Thr Tyr Pro Glu Asn Gly Arg Thr Phe His
        210                 215                 220

Leu Thr Arg Thr Leu Thr Val Lys Val Val Gly Ser Pro Lys Asn Ala
225                 230                 235                 240

Val Pro Pro Val Ile His Ser Pro Asn Asp His Val Val Tyr Glu Lys
                245                 250                 255

Glu Pro Gly Glu Glu Leu Leu Ile Pro Cys Thr Val Tyr Phe Ser Phe
            260                 265                 270

Leu Met Asp Ser Arg Asn Glu Val Trp Trp Thr Ile Asp Gly Lys Lys
        275                 280                 285

Pro Asp Asp Ile Thr Ile Asp Val Thr Ile Asn Glu Ser Ile Ser His
290                 295                 300

Ser Arg Thr Glu Asp Glu Thr Arg Thr Gln Ile Leu Ser Ile Lys Lys
                305                 310                 315                 320

Val Thr Ser Glu Asp Leu Lys Arg Ser Tyr Val Cys His Ala Arg Ser
            325                 330                 335

Ala Lys Gly Glu Val Ala Lys Ala Ala Lys Val Lys Gln Lys Gly Asn
        340                 345                 350

Arg Cys Gly Gln
        355

<210> SEQ ID NO 2
<211> LENGTH: 570
<212> TYPE: PRT
<213> ORGANISM: Homo sapiens

<400> SEQUENCE: 2

Met Thr Leu Leu Trp Cys Val Val Ser Leu Tyr Phe Tyr Gly Ile Leu
1               5                   10                  15

Gln Ser Asp Ala Ser Glu Arg Cys Asp Asp Trp Gly Leu Asp Thr Met
            20                  25                  30

Arg Gln Ile Gln Val Phe Glu Asp Glu Pro Ala Arg Ile Lys Cys Pro
        35                  40                  45

Leu Phe Glu His Phe Leu Lys Phe Asn Tyr Ser Thr Ala His Ser Ala
    50                  55                  60

Gly Leu Thr Leu Ile Trp Tyr Trp Thr Arg Gln Asp Arg Asp Leu Glu
65                  70                  75                  80

Glu Pro Ile Asn Phe Arg Leu Pro Glu Asn Arg Ile Ser Lys Glu Lys
                85                  90                  95

Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
        115                 120                 125

Leu Glu Val Val Gln Lys Asp Ser Cys Phe Asn Ser Pro Met Lys Leu
    130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                165                 170                 175

Trp Tyr Met Gly Cys Tyr Lys Ile Gln Asn Phe Asn Asn Val Ile Pro
            180                 185                 190
```

```
Glu Gly Met Asn Leu Ser Phe Leu Ile Ala Leu Ile Ser Asn Asn Gly
            195                 200                 205
Asn Tyr Thr Cys Val Val Thr Tyr Pro Glu Asn Gly Arg Thr Phe His
210                 215                 220
Leu Thr Arg Thr Leu Thr Val Lys Val Val Gly Ser Pro Lys Asn Ala
225                 230                 235                 240
Val Pro Pro Val Ile His Ser Pro Asn Asp His Val Val Tyr Glu Lys
                245                 250                 255
Glu Pro Gly Glu Glu Leu Leu Ile Pro Cys Thr Val Tyr Phe Ser Phe
            260                 265                 270
Leu Met Asp Ser Arg Asn Glu Val Trp Trp Thr Ile Asp Gly Lys Lys
            275                 280                 285
Pro Asp Asp Ile Thr Ile Asp Val Thr Ile Asn Glu Ser Ile Ser His
            290                 295                 300
Ser Arg Thr Glu Asp Glu Thr Arg Thr Gln Ile Leu Ser Ile Lys Lys
305                 310                 315                 320
Val Thr Ser Glu Asp Leu Lys Arg Ser Tyr Val Cys His Ala Arg Ser
                325                 330                 335
Ala Lys Gly Glu Val Ala Lys Ala Ala Lys Val Lys Gln Lys Val Pro
            340                 345                 350
Ala Pro Arg Tyr Thr Val Glu Leu Ala Cys Gly Phe Gly Ala Thr Val
            355                 360                 365
Leu Leu Val Val Ile Leu Ile Val Val Tyr His Val Tyr Trp Leu Glu
            370                 375                 380
Met Val Leu Phe Tyr Arg Ala His Phe Gly Thr Asp Glu Thr Ile Leu
385                 390                 395                 400
Asp Gly Lys Glu Tyr Asp Ile Tyr Val Ser Tyr Ala Arg Asn Ala Glu
                405                 410                 415
Glu Glu Glu Phe Val Leu Leu Thr Leu Arg Gly Val Leu Glu Asn Glu
            420                 425                 430
Phe Gly Tyr Lys Leu Cys Ile Phe Asp Arg Asp Ser Leu Pro Gly Gly
            435                 440                 445
Ile Val Thr Asp Glu Thr Leu Ser Phe Ile Gln Lys Ser Arg Arg Leu
            450                 455                 460
Leu Val Val Leu Ser Pro Asn Tyr Val Leu Gln Gly Thr Gln Ala Leu
465                 470                 475                 480
Leu Glu Leu Lys Ala Gly Leu Glu Asn Met Ala Ser Arg Gly Asn Ile
                485                 490                 495
Asn Val Ile Leu Val Gln Tyr Lys Ala Val Lys Glu Thr Lys Val Lys
            500                 505                 510
Glu Leu Lys Arg Ala Lys Thr Val Leu Thr Val Ile Lys Trp Lys Gly
            515                 520                 525
Glu Lys Ser Lys Tyr Pro Gln Gly Arg Phe Trp Lys Gln Leu Gln Val
            530                 535                 540
Ala Met Pro Val Lys Lys Ser Pro Arg Arg Ser Ser Ser Asp Glu Gln
545                 550                 555                 560
Gly Leu Ser Tyr Ser Ser Leu Lys Asn Val
                565                 570

<210> SEQ ID NO 3
<211> LENGTH: 270
<212> TYPE: PRT
<213> ORGANISM: Homo sapiens

<400> SEQUENCE: 3
```

```
Met Lys Pro Lys Met Lys Tyr Ser Thr Asn Lys Ile Ser Thr Ala Lys
 1               5                   10                  15

Trp Lys Asn Thr Ala Ser Lys Ala Leu Cys Phe Lys Leu Gly Lys Ser
                20                  25                  30

Gln Gln Lys Ala Lys Glu Val Cys Pro Met Tyr Phe Met Lys Leu Arg
                35                  40                  45

Ser Gly Leu Met Ile Lys Lys Glu Ala Cys Tyr Phe Arg Arg Glu Thr
 50                  55                  60

Thr Lys Arg Pro Ser Leu Lys Thr Gly Arg Lys His Lys Arg His Leu
 65                  70                  75                  80

Val Leu Ala Ala Cys Gln Gln Gln Ser Thr Val Glu Cys Phe Ala Phe
                85                  90                  95

Gly Ile Ser Gly Val Gln Lys Tyr Thr Arg Ala Leu His Asp Ser Ser
                100                 105                 110

Ile Thr Gly Ile Ser Pro Ile Thr Glu Tyr Leu Ala Ser Leu Ser Thr
                115                 120                 125

Tyr Asn Asp Gln Ser Ile Thr Phe Ala Leu Glu Asp Glu Ser Tyr Glu
 130                 135                 140

Ile Tyr Val Glu Asp Leu Lys Lys Asp Glu Lys Lys Asp Lys Val Leu
 145                 150                 155                 160

Leu Ser Tyr Tyr Glu Ser Gln His Pro Ser Asn Glu Ser Gly Asp Gly
                165                 170                 175

Val Asp Gly Lys Met Leu Met Val Thr Leu Ser Pro Thr Lys Asp Phe
                180                 185                 190

Trp Leu His Ala Asn Asn Lys Glu His Ser Val Glu Leu His Lys Cys
                195                 200                 205

Glu Lys Pro Leu Pro Asp Gln Ala Phe Phe Val Leu His Asn Met His
                210                 215                 220

Ser Asn Cys Val Ser Phe Glu Cys Lys Thr Asp Pro Gly Val Phe Ile
 225                 230                 235                 240

Gly Val Lys Asp Asn His Leu Ala Leu Ile Lys Val Asp Ser Ser Glu
                245                 250                 255

Asn Leu Cys Thr Glu Asn Ile Leu Phe Lys Leu Ser Glu Thr
                260                 265                 270

<210> SEQ ID NO 4
<211> LENGTH: 328
<212> TYPE: PRT
<213> ORGANISM: Homo sapiens
<220> FEATURE:
<221> NAME/KEY: SIGNAL
<222> LOCATION: (1)..(18)
<220> FEATURE:
<221> NAME/KEY: CHAIN
<222> LOCATION: (19)..(328)

<400> SEQUENCE: 4

Met Gly Phe Trp Ile Leu Ala Ile Leu Thr Ile Leu Met Tyr Ser Thr
 1               5                   10                  15

Ala Ala Lys Phe Ser Lys Gln Ser Trp Gly Leu Glu Asn Glu Ala Leu
                20                  25                  30

Ile Val Arg Cys Pro Arg Gln Gly Lys Pro Ser Tyr Thr Val Asp Trp
                35                  40                  45

Tyr Tyr Ser Gln Thr Asn Lys Ser Ile Pro Thr Gln Glu Arg Asn Arg
 50                  55                  60

Val Phe Ala Ser Gly Gln Leu Leu Lys Phe Leu Pro Ala Ala Val Ala
```

```
                65                  70                  75                  80
Asp Ser Gly Ile Tyr Thr Cys Ile Val Arg Ser Pro Thr Phe Asn Arg
                85                  90                  95

Thr Gly Tyr Ala Asn Val Thr Ile Tyr Lys Lys Gln Ser Asp Cys Asn
            100                 105                 110

Val Pro Asp Tyr Leu Met Tyr Ser Thr Val Ser Gly Ser Glu Lys Asn
            115                 120                 125

Ser Lys Ile Tyr Cys Pro Thr Ile Asp Leu Tyr Asn Trp Thr Ala Pro
        130                 135                 140

Leu Glu Trp Phe Lys Asn Cys Gln Ala Leu Gln Gly Ser Arg Tyr Arg
145                 150                 155                 160

Ala His Lys Ser Phe Leu Val Ile Asp Asn Val Met Thr Glu Asp Ala
                165                 170                 175

Gly Asp Tyr Thr Cys Lys Phe Ile His Asn Glu Asn Gly Ala Asn Tyr
            180                 185                 190

Ser Val Thr Ala Thr Arg Ser Phe Thr Val Lys Asp Glu Gln Gly Phe
        195                 200                 205

Ser Leu Phe Pro Val Ile Gly Ala Pro Ala Gln Asn Glu Ile Lys Glu
    210                 215                 220

Val Glu Ile Gly Lys Asn Ala Asn Leu Thr Cys Ser Ala Cys Phe Gly
225                 230                 235                 240

Lys Gly Thr Gln Phe Leu Ala Ala Val Leu Trp Gln Leu Asn Gly Thr
                245                 250                 255

Lys Ile Thr Asp Phe Gly Glu Pro Arg Ile Gln Gln Glu Glu Gly Gln
            260                 265                 270

Asn Gln Ser Phe Ser Asn Gly Leu Ala Cys Leu Asp Met Val Leu Arg
        275                 280                 285

Ile Ala Asp Val Lys Glu Asp Leu Leu Leu Gln Tyr Asp Cys Leu
    290                 295                 300

Ala Leu Asn Leu His Gly Leu Arg Arg His Thr Val Arg Leu Ser Arg
305                 310                 315                 320

Lys Asn Pro Ser Lys Glu Cys Phe
                325

<210> SEQ ID NO 5
<211> LENGTH: 556
<212> TYPE: PRT
<213> ORGANISM: Homo sapiens
<220> FEATURE:
<221> NAME/KEY: SIGNAL
<222> LOCATION: (1)..(18)
<220> FEATURE:
<221> NAME/KEY: CHAIN
<222> LOCATION: (19)..(556)

<400> SEQUENCE: 5

Met Gly Phe Trp Ile Leu Ala Ile Leu Thr Ile Leu Met Tyr Ser Thr
1               5                   10                  15

Ala Ala Lys Phe Ser Lys Gln Ser Trp Gly Leu Glu Asn Glu Ala Leu
            20                  25                  30

Ile Val Arg Cys Pro Arg Gln Gly Lys Pro Ser Tyr Thr Val Asp Trp
        35                  40                  45

Tyr Tyr Ser Gln Thr Asn Lys Ser Ile Pro Thr Gln Glu Arg Asn Arg
    50                  55                  60

Val Phe Ala Ser Gly Gln Leu Leu Lys Phe Leu Pro Ala Ala Val Ala
65                  70                  75                  80
```

-continued

```
Asp Ser Gly Ile Tyr Thr Cys Ile Val Arg Ser Pro Thr Phe Asn Arg
                85                  90                  95

Thr Gly Tyr Ala Asn Val Thr Ile Tyr Lys Lys Gln Ser Asp Cys Asn
               100                 105                 110

Val Pro Asp Tyr Leu Met Tyr Ser Thr Val Ser Gly Ser Glu Lys Asn
               115                 120                 125

Ser Lys Ile Tyr Cys Pro Thr Ile Asp Leu Tyr Asn Trp Thr Ala Pro
           130                 135                 140

Leu Glu Trp Phe Lys Asn Cys Gln Ala Leu Gln Gly Ser Arg Tyr Arg
145                 150                 155                 160

Ala His Lys Ser Phe Leu Val Ile Asp Asn Val Met Thr Glu Asp Ala
                165                 170                 175

Gly Asp Tyr Thr Cys Lys Phe Ile His Asn Glu Asn Gly Ala Asn Tyr
                180                 185                 190

Ser Val Thr Ala Thr Arg Ser Phe Thr Val Lys Asp Glu Gln Gly Phe
            195                 200                 205

Ser Leu Phe Pro Val Ile Gly Ala Pro Ala Gln Asn Glu Ile Lys Glu
            210                 215                 220

Val Glu Ile Gly Lys Asn Ala Asn Leu Thr Cys Ser Ala Cys Phe Gly
225                 230                 235                 240

Lys Gly Thr Gln Phe Leu Ala Ala Val Leu Trp Gln Leu Asn Gly Thr
                245                 250                 255

Lys Ile Thr Asp Phe Gly Glu Pro Arg Ile Gln Gln Glu Glu Gly Gln
                260                 265                 270

Asn Gln Ser Phe Ser Asn Gly Leu Ala Cys Leu Asp Met Val Leu Arg
            275                 280                 285

Ile Ala Asp Val Lys Glu Glu Asp Leu Leu Leu Gln Tyr Asp Cys Leu
            290                 295                 300

Ala Leu Asn Leu His Gly Leu Arg Arg His Thr Val Arg Leu Ser Arg
305                 310                 315                 320

Lys Asn Pro Ile Asp His His Ser Ile Tyr Cys Ile Ile Ala Val Cys
                325                 330                 335

Ser Val Phe Leu Met Leu Ile Asn Val Leu Val Ile Ile Leu Lys Met
                340                 345                 350

Phe Trp Ile Glu Ala Thr Leu Leu Trp Arg Asp Ile Ala Lys Pro Tyr
            355                 360                 365

Lys Thr Arg Asn Asp Gly Lys Leu Tyr Asp Ala Tyr Val Val Tyr Pro
            370                 375                 380

Arg Asn Tyr Lys Ser Ser Thr Asp Gly Ala Ser Arg Val Glu His Phe
385                 390                 395                 400

Val His Gln Ile Leu Pro Asp Val Leu Glu Asn Lys Cys Gly Tyr Thr
                405                 410                 415

Leu Cys Ile Tyr Gly Arg Asp Met Leu Pro Gly Glu Asp Val Val Thr
                420                 425                 430

Ala Val Glu Thr Asn Ile Arg Lys Ser Arg Arg His Ile Phe Ile Leu
            435                 440                 445

Thr Pro Gln Ile Thr His Asn Lys Glu Phe Ala Tyr Glu Gln Glu Val
            450                 455                 460

Ala Leu His Cys Ala Leu Ile Gln Asn Asp Ala Lys Val Ile Leu Ile
465                 470                 475                 480

Glu Met Glu Ala Leu Ser Glu Leu Asp Met Leu Gln Ala Glu Ala Leu
                485                 490                 495

Gln Asp Ser Leu Gln His Leu Met Lys Val Gln Gly Thr Ile Lys Trp
```

-continued

```
                    500                     505                     510
Arg Glu Asp His Ile Ala Asn Lys Arg Ser Leu Asn Ser Lys Phe Trp
        515                     520                     525

Lys His Val Arg Tyr Gln Met Pro Val Pro Ser Lys Ile Pro Arg Lys
    530                     535                     540

Ala Ser Ser Leu Thr Pro Leu Ala Ala Gln Lys Gln
545                     550                     555
```